United States Patent [19]
Feller et al.

[11] Patent Number: 5,897,492
[45] Date of Patent: Apr. 27, 1999

[54] CANDY TONGUE DEPRESSOR

[76] Inventors: Mitchell Dean Feller; Joanna Michelle Feller, both of 2508 Myrtle Ave., Sullivan's Island, S.C. 29482

[21] Appl. No.: 09/137,856

[22] Filed: Aug. 21, 1998

[51] Int. Cl.⁶ .............................. A61B 17/00; B65D 83/10
[52] U.S. Cl. ............................................. 600/240; 206/363
[58] Field of Search .................... 600/240, 235, 600/201; 206/363, 828, 810

[56] References Cited

U.S. PATENT DOCUMENTS

| | | | |
|---|---|---|---|
| D. 359,556 | 6/1995 | Hale et al. | D24/136 |
| 1,502,006 | 7/1924 | Alvord . | |
| 1,586,137 | 5/1926 | Zanath . | |
| 2,425,945 | 8/1947 | Leach . | |
| 2,857,908 | 10/1958 | Cornfield | 600/240 |
| 3,867,927 | 2/1975 | Hergott | 428/15 |
| 4,041,937 | 8/1977 | Diaz | 600/240 |
| 4,451,329 | 11/1985 | Harris et al. | 424/22 |
| 5,503,842 | 4/1996 | Fazan et al. | 424/443 |
| 5,553,627 | 9/1996 | Newkirk | 600/240 X |
| 5,634,885 | 6/1997 | Kiro | 600/240 |
| 5,702,742 | 12/1997 | Jones | 426/115 |

*Primary Examiner*—Jeffrey A. Smith
*Attorney, Agent, or Firm*—Harleston Law Firm; Kathleen M. Harleston

[57] ABSTRACT

A candy-tongue depressor for encouraging the cooperation of a child or teenager during an oral examination by a medical practitioner is provided. The device comprises, in combination: (a) a thin, flat, nonedible stick with a longitudinal axis; the nonedible stick having a distal end for grasping by the medical practitioner; and a proximal end for contacting the tongue of a patient; and (b) a thin layer of candy which covers the proximal end, but not the distal end, of the nonedible stick. A combination candy tongue depressor and flexible, reclosable, translucent wrapper is also provided.

16 Claims, 3 Drawing Sheets

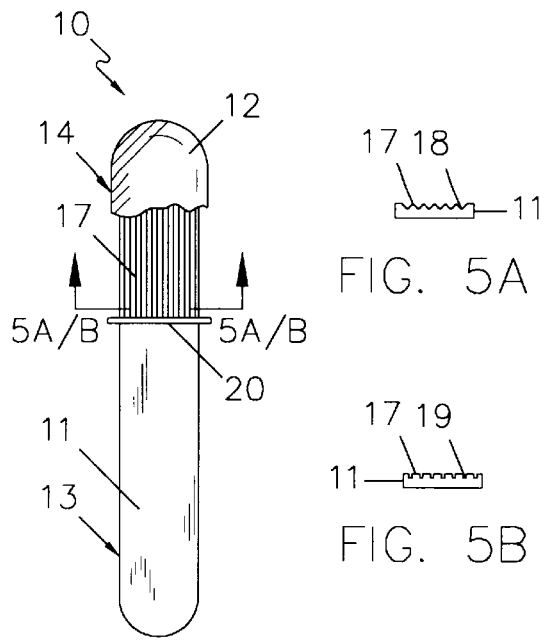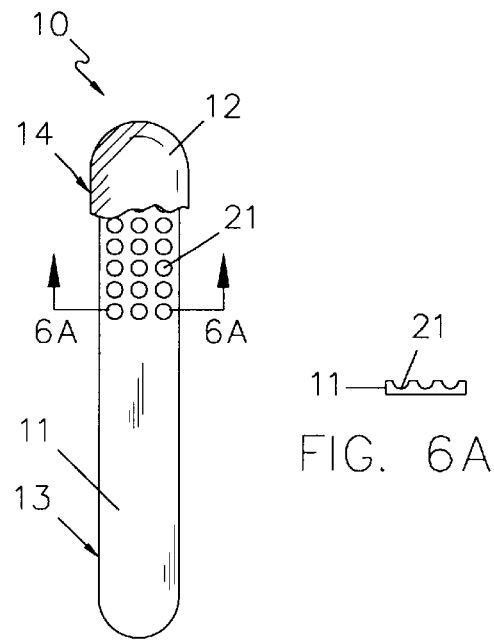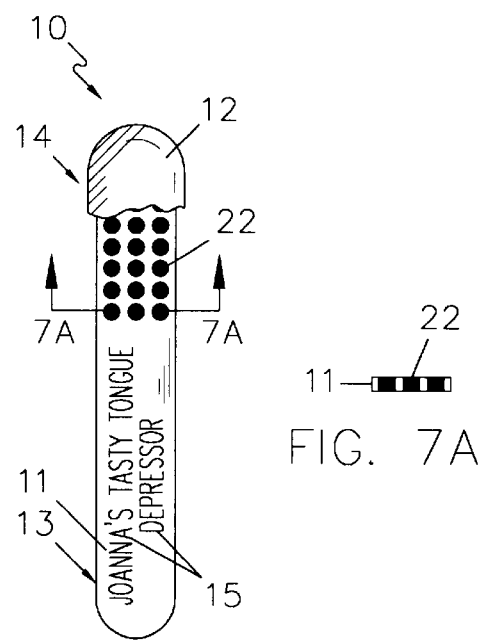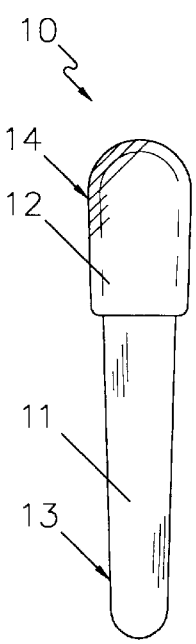

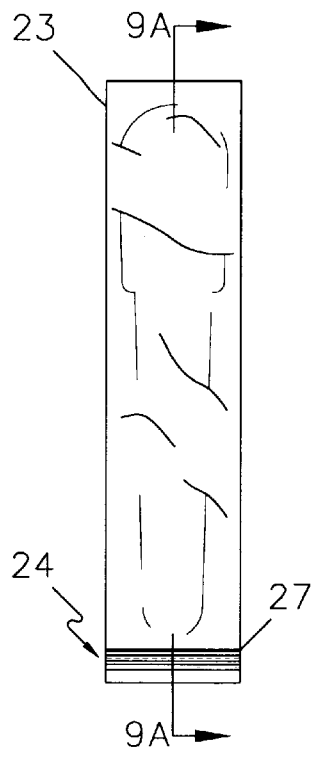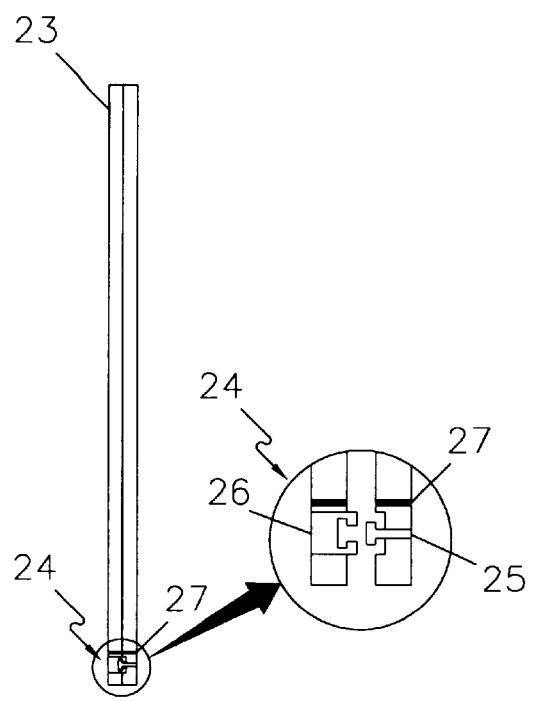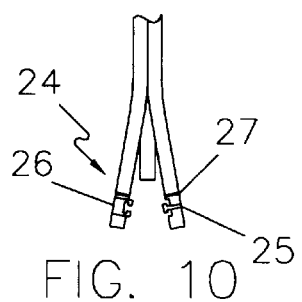
FIG. 9
FIG. 9A
FIG. 10

CANDY TONGUE DEPRESSOR

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Technical Field

The present device is a candy-tongue depressor comprising, in combination, a tongue depressor, and a thin layer of candy which covers the proximal, but not the distal end, of the tongue depressor.

2. Background Information

One of the single most important, and yet dreaded, parts of the physical examination of a child is that of the oral cavity. Almost every physical examination performed by a family physician or pediatrician on a well or sick child includes an oral examination. The mouth and throat are also normally examined during most adult visits to the doctor or other medical practitioner. While adults will usually accept an oral exam, the majority of children do not. The sight of an innocuous tongue depressor arriving in front of a small child's face often prompts the child's jaw to snap shut and remain locked despite efforts by the adults in the examination room to pry it open. Every practitioner has his or her own favorite way to coax, compel, or coerce open the tightly clamped teeth of children from six months to 16 years of age. Many children must be restrained by the parent or other caregiver present during the examination. A few children require restraint by several adults. Some medical practitioners harness the patient in a papoose board, which confines the child's arms and legs but does not open the jaws. An oral examination on a child is thus often traumatic for both the child and the medical practitioner.

The tongue depressors of the present invention are coated with candy or the like at one end to make them more attractive to patients. Children in general will be more interested in putting these tongue depressors into their mouths to taste the candy, thus reducing the anxiety associated with oral examinations. The child is empowered by being offered a choice of candy coating flavors prior to the examination. It is believed that the small amount of candy on the candy tongue depressor will not interfere with oral examinations or the taking of throat cultures. The child may take the coated tongue depressor home after the examination.

BRIEF SUMMARY OF THE INVENTION

The present invention is a candy-tongue depressor device for encouraging the cooperation of a child or teenager during an oral examination by a medical practitioner. The device comprises, in combination:

(a) a thin, flat, nonedible stick with a longitudinal axis; the nonedible stick having a distal end for grasping by the medical practitioner; and a proximal end for contacting the tongue of a patient; and (b) a thin layer of candy which covers the proximal end, but not the distal end, of the nonedible stick.

A combination candy tongue depressor and flexible, reclosable, translucent wrapper is also provided.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein:

FIG. 5 is a front view of a grooved candy tongue depressor according to the present invention;

FIGS. 5A & 5B are alternative cross-sections of the candy tongue depressor of FIG. 5, each taken along line 5A/B—5A/B;

FIG. 6 is a front view of a dimpled candy tongue depressor according to the present invention;

FIG. 6A is a cross-section of the candy tongue depressor of FIG. 6, taken along line 6A—6A;

FIG. 7 is a front view of a perforated candy tongue depressor according to the present invention;

FIG. 7A is a cross-section of the candy tongue depressor of FIG. 7, taken along line 7A—7A;

FIG. 8 is a front view of an asymmetrical candy tongue depressor according to the present invention;

FIG. 9 is a front view of a candy tongue depressor and wrapper according to the present invention;

FIG. 9A is a longitudinal cross-section of the candy tongue depressor wrapper of FIG. 9; and FIG. 10 is a partial longitudinal cross-section of the candy tongue depressor and wrapper of FIG. 9.

DETAILED DESCRIPTION OF THE INVENTION

Figure 1:
FIG. 1 is a perspective view of a preferred embodiment of a candy tongue depressor according to the present invention.

In the following description, like reference characters designate like or corresponding parts throughout the several views. Also, in the following description, it is to be understood that such terms as "front," "back," "face," and the like are words of convenience and are not to be construed as limiting terms. Referring in more detail to the drawings, the invention will now be described.

Figure 1A:
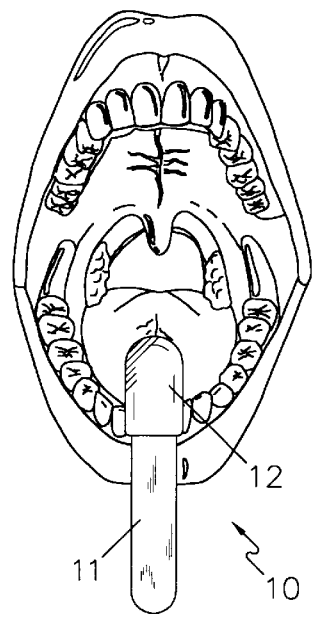
FIG. 1A is a perspective view of the candy tongue depressor of FIG. 1.

Referring to FIG. 1, a candy tongue depressor 10 according to the present invention comprises, in combination: a) a thin, flat, nonedible stick 11 with a longitudinal axis, and b) a thin layer of candy 12 which is adhered to one end of the nonedible stick 11. This candy tongue depressor device 10 is for encouraging the cooperation of a child or teenager during an oral examination by a medical practitioner. As shown in FIGS. 1 and 1A, the candy portion 12 of the device 10 is inserted into the mouth of the patient. The nonedible stick 11 is held by the medical practitioner to manipulate the patient's tongue or cheeks. As shown in FIG. 1A, the candy portion 12 is placed in the middle region on the top of the patient's tongue and is pressed down by the practitioner for a view of the throat and tonsils. This also gives the patient a taste of the candy portion 12.

Figure 2:
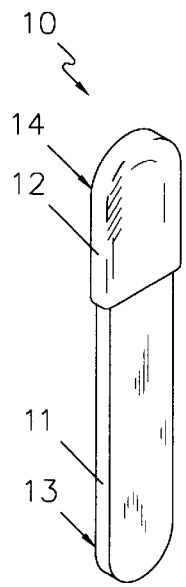
FIG. 2 is a perspective view of a preferred embodiment of a candy tongue depressor according to the present invention.

Referring to FIG. 2, the nonedible stick 11 has a distal end 13 for grasping by the medical practitioner; and a proximal end 14 for contacting the tongue of a patient. The proximal end 14 is inserted in the patient's mouth during an oral examination. The candy portion 12 preferably extends no more than about 2 centimeters, more preferably no more than about 50 millimeters, most preferably no more than about 2 millimeters, beyond the boundaries of the nonedible stick portion (on each side). This is because too much candy at the end of the depressor could block the physician's view of the mouth and throat, prompt a gag reflex, or cause other problems. The amount of candy on the candy tongue depressor is preferably between about 5 and about 100, more preferably between about 20 and about 30, grams on each device. This amount is most preferably spread evenly over the proximal ⅓ to ½ of the stick. This minimal amount of candy is enough to act as a reward for the child and yet is not enough to interfere with the oral examination, a healthy diet, clean teeth, or parental limitations. The present invention most preferably consists essentially of the combination of the thin, flat nonedible stick 11 with a longitudinal axis, and the thin layer of candy 12 which is adhered to the proximal end 14, but not the distal end 13, of the nonedible stick 11.

Figure 3:
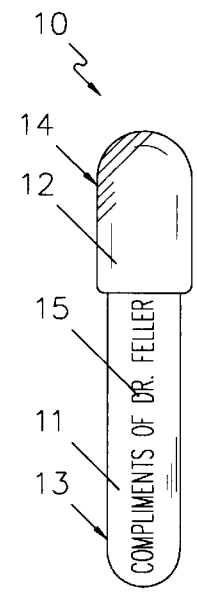
FIG. 3 is a front view of a candy tongue depressor according to the present invention.
Figure 4:
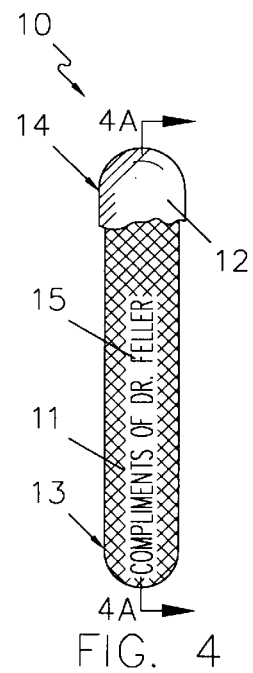
FIG. 4 is a front view of a striated candy tongue depressor according to the present invention.

As shown in FIG. 3, the candy tongue depressor 10 preferably includes a message 15 on the nonedible stick 11. The message 15 can be written on, stamped in, or adhered to a portion of one face of the nonedible stick 11. Preferably, the message 15 is stamp printed onto the nonedible stick 11. The message 15 may be located on the proximal end 14 of the nonedible stick 11 beneath the candy 12 so that it becomes visible to the child after the candy is substantially licked off the nonedible stick portion 11. The message is preferably: 1) a joke, fortune, or message of good will (preferably underneath the proximal portion of the nonedible stick); 2) a picture, logo, icon or trademarked likeness of a popular children's figure from a cartoon, movie, book, toy or other source; 3) an advertisement for the confectioner or the manufacturer; 3) the doctor's name or office (e.g., "Compliments of Dr. Feller," as shown in FIGS. 3 and 4); or 4) a space for the child's name to be written by the practitioner. The latter three are preferably on the distal portion of the nonedible stick. The present candy tongue depressors are preferably displayed in a visible location in the practitioner's examination room in, for example, round glass jars so that the various colors would attract children's attention and be pleasing to them.

In FIGS. 4 through 7, the candy 12 is cut away to show the portion of the nonedible stick 11 which lies underneath the candy 12 The candy is preferably applied to the substrate, which is the proximal portion of the nonedible stick 11, by coating. The nonedible stick is preferably wooden, but can be plastic or another smooth, inexpensive, sanitary material which is suitable for use in the mouth. The child or teenager is preferably a well or sick pediatric patient between the ages of 6 months and 19 years who is about to undergo an oral examination.

Figure 4A:
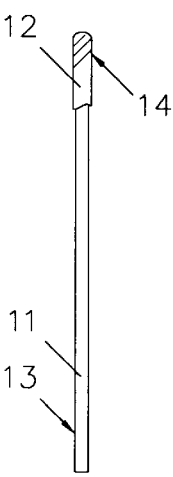
FIG. 4A is a side view of the candy tongue depressor of FIG. 4.

FIGS. 4 through 8 show alternate embodiments of the present invention. In FIG. 4, the candy tongue depressor is striated by cross-hatching 16 on the nonedible stick, which is preferably done during manufacture. The nonedible stick may be striated or otherwise marked in whole as shown in FIG. 4, or in part, as shown in FIGS. 5 through 7. It may be easier during manufacture to striate both faces (i.e., the back and front) of the nonedible stick 11 rather than a portion of it. The markings are preferably on one face, front or back, of the nonedible stick 11. As shown in the FIG. 4A side view, there are no striations along the thin sides of the nonedible stick because there is no need for additional surface area along the sides. A striated or otherwise marked (cut) nonedible stick allows for increased substrate at the top (proximal portion) of the stick to which the candy 12 more easily adheres. Marking the distal portion of the nonedible stick is also advantageous in that it is more easily gripped by the medical practitioner or, later, the child, particularly when the fingers of either are wet or sticky. During the medical exam, the striated or otherwise marked portion of the nonedible stick does not touch the tongue of the child; the candy portion does.

As shown in the alternate embodiment of FIG. 5, the nonedible stick 11 portion has striations 17 on the proximal portion 14 of its front face. The nonedible stick 11 preferably comprises a low ridge 20 adjacent to the candy layer 12. This ridge helps to confine the candy and saliva somewhat to the proximal, candy end of the stick while the candy tongue depressor is in the mouth, and to separate the candy and saliva from the distal, clean end of the stick, which is being held by the medical practitioner. The low ridge 20 is preferably less than about 10 millimeters in width, and about 10 millimeters deep. The depth is the distance from the surface of the nonedible stick 11 to the top of the ridge 20. The ridge 20 preferably extends around the circumference of the stick it at the edge of the candy coating 12, which is at a point between about ½ and ⅓ along the stick portion 11.

FIGS. 5A and 5B show alternate (lateral) cross-sections of the grooved candy tongue depressor of FIG. 5, taken along line 5A/B—5A/B. The front face of the nonedible stick 11 is shown at the top of the cross-sections of FIGS. 5A and 5B. FIG. 5A shows V-shaped notches 18 and FIG. 5B shows squared-off grooves 19.

Referring now to the alternate embodiment of the invention shown in FIG. 6, the proximal end 14 of the nonedible stick 11 comprises a plurality of dimples 21. The dimples 21 increase the surface area and serve as small reservoirs so that slightly more candy coats the nonedible stick 11 without interfering with the width of the candy layer 12. The candy layer is enough to act as a reward but not so much as to impede an oral examination.

FIG. 6A shows a (lateral) cross-section of the dimpled candy tongue depressor of FIG. 6, taken along line 6A—6A, with the front face of the nonedible stick shown at the top of the cross-section. The FIG. 6A cross-section shows a row of three dimples 21 across one face of the nonedible stick 11.

Referring now to the alternate embodiment of the invention shown in FIG. 7, the nonedible stick 11 comprises perforations 22 on the proximal portion 14 of the nonedible stick 11. The perforations 22, which may be in rows or randomly placed, increase the surface area and collect additional candy without interfering with the width of the candy layer 12. Thus, the candy layer is enough to act as a reward but not so much as to impede the oral examination. Although the candy-filled perforations add interest to the child and prolong the pleasant process of licking off the candy, they add difficulty to the manufacturing process, so this embodiment is less preferred. The device shown in FIG. 7 includes an example of a suitable message 15: "Joanna's Tasty Tongue Depressor."

FIG. 7A shows a cross-section of the candy tongue depressor of FIG. 7, taken along line 7A—7A. A row of three perforations 22 is shown across the face of the nonedible stick 11.

The nonedible stick 11 of the present invention is preferably between about 4 and about 8 inches in length, between about ½ and about 1 inch in width, and between about 1/10 and about ¼ inch in depth. It is preferably of an even width all the way along the nonedible stick.

FIG. 8 shows a less preferred embodiment of the present invention: an asymmetrical candy tongue depressor. The asymmetrical shape adds interest and more easily distinguishes the distal handle end from the proximal candy end on sight. The candy 12 is preferably at the wider end of the depressor.

The candy used in the present invention must be of the proper consistency to evenly and thinly coat the tongue depressor during manufacture. The coating must adhere to the wood but not stick to any wrappings. The candy coating must remain in place without melting or spoiling during storage and transport. The candy 12 preferably comprises caramel, chocolate, or fruit flavored candy. The top ¼ to ¾, preferably ⅓ to ½, of the tongue depressor comprises the candy covering, which is on one or, preferably, both sides of the depressor. The bottom portion (¾ to ¼) of the tongue depressor is free of the coating because it must be held in a sanitary manner by the medical practitioner who is conducting the oral examination. By candy is meant a comestible confection. A combination of candies may be used, either in a mixture or in layers (e.g. candy over a bubble gum core) on the nonedible stick.

Candy with a melting point above room temperature is preferred. Soft candy may be covered by an edible shell. The shell may be a heat tolerant coating to prevent the candy from melting in hot environments such as inside a car on a summer day. Soft candy which melts slowly in the mouth but not at room temperature is preferred so that the candy coating remains intact during shipping and does not make a mess when the wrapper is removed, yet it melts slowly in the warmer temperatures of the mouth so that it can be tasted during the oral examination. The candy 12 preferably has a melting point between about 98 and 101, preferably 98.6, degrees Fahrenheit.

In the present invention, the candy is not substantially confined within the inner bounding surfaces of an area within the nonedible stick portion. Instead, the candy in the present invention coats a portion of the outside of the nonedible stick. When a portion of the nonedible stick 11 is striated, grooved, perforated (fenestrated), dimpled, or otherwise marked, candy may also extend into the crevices or pockets thus created.

Candy is gaining acceptance as a fashionable, acceptable treat and confectioners are creating sophisticated images for their products. There are also a number of recently introduced candy alternatives, low calorie additives, low fat substitutes, and artificial/no calorie sweeteners. These can be used to substitute for part or all of the candy used in the present invention. They include aspartame or other sugar substitutes, polydextrose for lower calorie products, caprenin instead of traditional dairy and saturated fats, and even the addition of vitamins, such as Vitamin C, or organic ingredients, such as honey. Conventional additives may also be included to maintain the freshness of the candy.

FIGS. 9–10 shows a device for encouraging the cooperation of a child or teenager during an oral examination by a medical practitioner, the device comprising, in combination:

(a) a candy tongue depressor, comprising: a thin, flat, nonedible stick 11 with a longitudinal axis; the nonedible stick 11 having a distal end 13 for grasping by the medical practitioner; and a proximal end 14 for contacting the tongue of a patient; and a thin layer of candy 12 which covers the proximal end 14, but not the distal end 13, of the nonedible stick 11; and (b) a flexible, reclosable, translucent wrapper 23 for removably enclosing the candy tongue depressor, the wrapper 23 having a longitudinal axis and comprising: an opening with a width slightly greater than the width of the candy tongue depressor, and a reclosable locking mechanism 24; and wherein the reclosable locking mechanism 24 is adjacent to the opening and comprises a male member 25 and a female member 26 which snap together.

The wrapper is preferably odorized and colorized. The (odor and/or) color of the wrapper may match the candy flavor inside, e.g., purple for a grape flavored candy layer. The wrapper protects the candy tongue depressor until it is removed and used by the medical practitioner. The wrapper should only be removed immediately prior to use in order to keep it clean. The wrapper would preferably be slightly longer, more preferably about one inch longer, and slightly wider than the device. The wrapper is preferably between about 5 and 9 inches in length, and about 1 and 2 inches in width. It is preferably only as thick as several pieces of the wrapper paper.

FIG. 9A is a longitudinal cross-section of the wrapper of FIG. 9 and shows an enlarged view of the reclosable locking mechanism 24. The reclosable locking mechanism 24 comprises a male member 25 and a female member 26 which snap together. Immediately below the reclosable locking mechanism 24 is a thin row of adhesive 27, which provides a relatively permanent seal until the wrapper 23 is opened by the medical practitioner. The wrapper 23 is preferably opened at one end by using both hands to pull apart the adhered opposing edges of the wrapper. The distal, clean end of the stick 11 is then grasped by the practitioner and the wrapper 23 is pulled off. This minimizes contact with the candy portion 12. The wrapper may then be used for storage of the candy tongue depressor before eating or to dispose of the nonedible stick 11 after the candy is eaten. The child or teenager may insert the candy tongue depressor in the wrapper and close it by squeezing the reclosable locking mechanism 24. This snaps the male member 25 into the female member 26. The wrapper can be opened again by pulling the two edges of the wrapper apart. A portion of a partially opened wrapped is shown in FIG. 10.

The present "Tasty Tongue Depressor" invention has many advantages, including the following.

1) It empowers pediatric patients by permitting them to select the color and flavor of candy tongue depressor prior to the actual oral examination.

2) It gives the child a sense of control. By being permitted to chose the color and flavor of his or her Tasty Tongue Depressor, the child is given a sense of control and ownership.

3) It adds an element of fun to the examination process. This is an advantage for both the patient and the practitioner. By facilitating communication between the doctor and patient, it makes for a more thorough physical examination. A brief amount of time is used up-front in the examination period to pleasantly discuss the choice of candy rather than being unpleasantly wasted trying to coerce the child's mouth open a few minutes further into the exam.

4) It enables the physician or other practitioner to immediately reward, and thus reinforce, the child for cooperative behavior. This is more advantageous than the traditional reward of a sucker or sticker at the check-out window in the doctor's office, which is not immediate and is often not associated by the child with any particular behavior.

5) It sets the stage for a discussion of childhood nutrition and the place of candy in a healthful diet. The present invention provides a seamless transition into a discussion of nutrition and the place of certain foods, such as sweets and saturated fats, within a healthy diet. This discussion is often more meaningful to a child when it is presented by the examining physician, who is often considered by the child to be an authority figure to whom even the parents must answer.

The choice of candies can be influenced by peer pressures and what is considered "cool" in contemporary culture, which is affected by the opinions of the child's siblings and friends. Parental attitudes about what is acceptable and healthy must be taken into account. Societal attitudes about fun and reward are also involved. The present invention uses these associations to facilitate the doctor's examination of the mouth and throat. The "Tasty Tongue Depressor" turns what was a dreaded experience into an anticipated part of the visit to the doctor (or other medical practitioner), in which the child is a willing participant. Since the child is involved in the selection of his or her Tasty Tongue Depressor, which (s)he can keep and eat, (s)he is more likely to cooperate with the examination.

It is believed that the Tasty Tongue Depressor will not interfere with a throat culture or a standard test for streptococcal bacteria, because swabs of the posterior pharyngeal region or lateral soft tissues and tonsils are taken for those tests. To take a culture, most physicians use one hand to hold down the tongue with the proximal portion of the depressor, and use the other hand to pass the swab over the above-mentioned areas. The tongue depressor is placed on the middle, posterior portion of the tongue to hold the tongue on the floor of the mouth while the culture is being taken. Most standard microbiological tests for oral examinations are now conducted in the primary care physician's office.

Confectioners have long known that children are leading consumers and trend setters in that they strongly influence purchases by their parents. Children apparently see candy in a very personal light. A piece of candy is small and inexpensive enough for a child to feel complete ownership of it. Every child is an expert on candy. They enjoy the whole process of selecting, purchasing, carrying, sequestering, eating, and even trading and sharing their candy. Children gain control by influencing their parents to buy candy, and parents, baby-sitters, and other caregivers gain control by offering it as a reward for good behavior. Candy generates joy, fun, and excitement. It is associated with vacations, entertainment (e.g. movies), birthdays, holidays like Christmas, Easter, and Halloween, and with special persons like grandparents. Most children know that they are likely to get candy when they are "good." The child who visits the doctor's or dentist's office often knows exactly where the candy/toy treasure box is and they often recall what is in the box and what treat they took away at their last visit. Here, it is believed that the child will associate the doctor's visit with other experiences, such as vacations and celebrations, which have been positive and memorable. Thus the Tasty Tongue Depressor helps to transform a visit to the doctor into an experience the child will cheerfully anticipate.

While preferred embodiments of the invention have been described using specific terms, this description is for illustrative purposes only. It will be apparent to those of ordinary skill in the art that various modifications may be made without departing from the spirit or scope of the invention, and that such modifications are intended to be within the scope of the present invention.

What is claimed is:

1. A candy-tongue depressor device for encouraging the cooperation of a child or teenager during an oral examination by a medical practitioner, the device comprising in combination:
    (a) a thin, flat, nonedible stick with a longitudinal axis; the nonedible stick having a distal end for grasping by the medical practitioner; and a proximal end for contacting the tongue of a patient; and
    (b) a thin layer of candy which covers the proximal end, but not the distal end, of the nonedible stick; and
wherein the nonedible stick comprises a plurality of dimples or grooves.

2. A device according to claim 1, wherein the nonedible stick is wood, and the candy layer extends no more than about 2 centimeters beyond the boundaries of the nonedible stick.

3. A device according to claim 2, wherein a substantial amount of the front and back surfaces of the nonedible stick are striated.

4. A device according to claim 2, wherein the device consists essentially of the nonedible stick and the candy layer.

5. A candy-tongue depressor device for encouraging the cooperation of a child or teenager during an oral examination by a medical practitioner, the device comprising in combination:
    a) a thin, flat, nonedible stick with a longitudinal axis; the nonedible stick having a distal end for grasping by the medical practitioner; and a proximal end for contacting the tongue of a patient; and
    (b) a thin layer of candy which covers the proximal end, but not the distal end, of the nonedible stick; and
wherein the nonedible stick comprises a low ridge bounding the edge of the candy layer.

6. A device according to claim 5, wherein the nonedible stick is wood, and the candy layer extends no more than about 2 centimeters beyond the boundaries of the nonedible stick, and wherein the device further comprises a flexible, translucent wrapper removably enclosing the nonedible stick and the candy layer.

7. A device according to claim 6, wherein the nonedible stick is between about 4 and about 8 inches in length, between about ½ and about 1 inch in width, and between about 1/10 and about ¼ inch in depth.

8. A device according to claim 7, wherein the proximal one half to one third of the nonedible stick is coated with a sticky, soft candy or candy substitute.

9. A device according to claim 8, further comprising a message on the nonedible stick.

10. A device according to claim 9, wherein the nonedible stick is striated, dimpled or perforated at its proximal end under the candy layer.

11. A device according to claim 8, comprising between about 1 and about 100 grams of candy, the candy layer being spread evenly over the proximal ⅓ to ½ of the nonedible stick.

12. A device according to claim 5, wherein the candy comprises aspartame or other sugar substitutes, polydextrose, caprenin, vitamins, or organic ingredients.

13. A device according to claim 5, wherein a substantial amount of the candy in the candy layer has a melting point between about 98 and 101 degrees Fahrenheit.

14. A device according to claim 5, wherein the candy comprises caramel, chocolate, or fruit flavored candy.

15. A device according to claim 14, wherein the low ridge is less than about 10 millimeters in width and about 10 millimeters deep.

16. A device for encouraging the cooperation of a child or teenager during an oral examination by a medical practitioner, the device comprising, in combination:

(a) a candy tongue depressor, comprising: a thin, flat, nonedible stick with a longitudinal axis; the nonedible stick having a distal end for grasping by the medical practitioner; and a proximal end for contacting the tongue of a patient; and a thin layer of candy which covers the proximal end, but not the distal end, of the nonedible stick; and (b) a flexible, reclosable, translucent wrapper for removably enclosing the candy tongue depressor, the wrapper having a longitudinal axis and comprising: an opening with a width slightly greater than the width of the candy tongue depressor, and a reclosable locking mechanism; and wherein the reclosable locking mechanism is adjacent to the opening and comprises a male member and a female member which snap together.

* * * * *